US006908897B2

(12) United States Patent
Brandenburg et al.

(10) Patent No.: US 6,908,897 B2
(45) Date of Patent: Jun. 21, 2005

(54) COVALENTLY BRIDGED INSULIN DIMERS

(75) Inventors: Dietrich Brandenburg, Reichelsheim (DE); Chantalle Havenith, Hofheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 82 days.

(21) Appl. No.: 09/934,766

(22) Filed: Aug. 23, 2001

(65) Prior Publication Data

US 2002/0160938 A1 Oct. 31, 2002

Related U.S. Application Data

(63) Continuation of application No. PCT/EP00/01530, filed on Feb. 24, 2000.

(30) Foreign Application Priority Data

Feb. 24, 1999 (DE) .......................................... 199 08 041

(51) Int. Cl.[7] ........................ A61K 38/28; C07K 17/00; C12P 21/06
(52) U.S. Cl. ................ 514/3; 514/4; 514/866; 530/303; 530/304; 530/402; 435/68.1; 435/810
(58) Field of Search ................................ 514/3, 4, 866; 530/303, 304, 402; 435/68.1, 810

(56) References Cited

FOREIGN PATENT DOCUMENTS

WO  WO 95/05187  2/1995

OTHER PUBLICATIONS

Deppe et al., Naunyn–Schmiedenberg's Archives of Pharmacology, vol. 35, No. 2, pp. 213–217, Aug. 1994.*
Leyer et al., International Journal of Peptide & Protein Research, vol. 46, No. 5, pp. 397–407, Nov. 1995.*
Schuttler et al., Hoppe–Seyler's Zeistschrift Fur Physiologische Chemie, vol. 363, No. 3, 317–330, Mar. 1982.*
Deppe, C. et al., "Structure–activity relationship of covalently dimerized insulin derivatives: correlation of partial agonist efficacy with cross–linkage at lysine B29," Naunyn–Schmiedeberg's Archives of Pharmacology, vol. 350, No. 2, p. 213–217 (Aug. 1994).
Leyer, Sigmar, et al., "The role of the C–terminus of the Insulin B–chain in modulating structural and functional properties of the hormone," International Journal of Peptide & Protein Research, vol. 46, No. 5, p. 397–407 (Nov. 1995).
Shojaee–Moradie, F. et al, "Demonstration of a relatively hepatoselective effect of covalent insulin dimers on glucose metabolism in dogs," Diabetologia, vol. 38, No. 9, p. 1007–1013.
Schüttler, A., et al., "Preparation of Properties of Covalently Linked Insulin Dimers," Hoppe–Seyler's Zeitschrift Für Physiologische Chemie, vol. 363, No. 3, p. 317–330 (Mar. 1982).

* cited by examiner

*Primary Examiner*—Jon Weber
*Assistant Examiner*—Abdel A. Mohamed
(74) *Attorney, Agent, or Firm*—William Coppola

(57) ABSTRACT

Provided herein is a heretofore unknown insulin analogue, a pharmaceutical composition comprising such an insulin analogue, as well as processes for preparing such an insulin analogue and such a pharmaceutical composition.

16 Claims, No Drawings

COVALENTLY BRIDGED INSULIN DIMERS

CROSS REFERENCE TO RELATED APPLICATIONS

This application is a continuation of International Application No. PCT/EP00/01530, filed Feb. 24, 2000, which is incorporated by reference herein and claims the priority of DE 199 08 041.0 filed Feb. 24, 1999, which is incorporated by reference herein.

The invention relates to novel insulin analogues and to a pharmaceutical comprising such insulin analogues, a process for producing a pharmaceutical for the treatment of diabetes, and a process for the preparation of the insulin analogues.

The proteohormone insulin is produced in the β cells of the islets of Langerhans. Its most important physiological effect includes the reduction in the blood glucose level. Insulin deficiency leads to the complex pathological state of diabetes mellitus (type I) which is characterized by deviant glucose metabolism.

Diabetes mellitus is treated by employing insulin and insulin analogues in pharmaceutical preparations. In the most widely used form of therapy, the replacement therapy, insulin is administered subcutaneously. The commonest side effect of this is hypoglycemia (low blood glucose level). Despite the continuous development of pharmaceutical preparations of insulin for diabetes therapy there is a continuing search for novel insulin analogues which are promising in relation to their efficacy in combination with the reduction in side effects. Thus, for example, a fast-acting "insulin lispro" was developed (EP 0 383 472 B1) by transposing the amino acids proline$^{B28}$ and lysine$^{B29}$. There has likewise been development of a long-acting insulin derivative by fatty acid acylation of the ε-amino group of lysine$^{B29}$ (J. Markussen, S. Havelund, P. Kurtzhals, A. A. Andersen, J. Halstrøm, E. Hasselager, U. D. Larsen, U. Ribel, L. Schäffer, K. Vad, I. Jonassen, Diabetologia 1996, 39, pp. 281–288). Although it is possible to influence the time course of the action of insulin by such modifications of the native structure of human insulin, considerable problems are still not solved: there is still no insulin analogue which can be used for therapy and permits, through even only partial tissue specificity, in particular hepatoselectivity, a more targeted therapy appropriate for the physiological conditions. Nor has there been disclosure of an analogue which, as a result of greater potency, could be employed in smaller amounts than human insulin or animal insulin with the native structure.

All the insulins employed for treating diabetes are always monomeric insulin molecules with a molecular mass of about 6 000. All monomeric insulin analogues and derivatives have proved to be partial or complete insulin agonists (S. Gammeltoft, Physiol. Rev. 1984, 64, p. 1321) and show a close correlation between receptor binding and triggering of the biological signal. Only in a few cases, such as, for example, in the case of covalently bridged insulin dimers, has a discrepancy between receptor binding and biological activity been observed (A Schüttler, D. Brandenburg, Hoppe Seyler's Z. Physiol. Chem. 1982, 363, pp.317–330, M. Weiland, C. Brandenburg, D. Brandenburg, H. G. Joost, Proc. Natl. Acad. Sci. USA 1990 87, pp. 1154–1158). In addition, insulin dimers have proved useful for differentiating insulin receptors in different tissues (M. Breiner, M. Weiland, W. Becker, D. Müller-Wieland, R. Streicher, M. Fabry, H. G. Joost, Molecular Pharmacology 1993, 44, pp. 271–276). They are thus of fundamental importance for diagnosis in pathological cases.

All the dimers described to date involve covalent bridging of two insulins in their native length. Insulin dimers are in principle of particular interest for therapy because they show a relative hepatoselectivity in animal experiments (demonstrated for B1,B1'-suberoyl-insulin dimer with native insulin structure, F. Shojaee-Moradie, N. C. Jackson, M. Boroujerdi, D. Brandenburg, P. H. Sönksen, R. H. Jones, Diabetologia 1995, 38, pp. 1007–1013) and thus make a more physiological reduction in the blood glucose level possible than all insulins employed at present in diabetes therapy. The B1,B1'-suberoyl-insulin dimer employed therein has, however, a considerably lower bioactivity in vitro than receptor binding (28.8% compared with 157–199%, M. A. Tatnell, R. H. Jones, K. P. Willey, A. Sch üttler, D. Brandenburg, Biochem. J. 1983, 216, pp. 687–694). The ratio of bioactivity to receptor binding is thus very low at 0.15–0.18. We are not aware of an application or further development of these findings in the direction of diabetes therapy.

We have now designed and synthesized novel insulin dimers which, by reason of their properties, are promising in relation to a solution to the abovementioned problems and an improved diabetes therapy and are also referred to as insulin analogues hereinafter. In this connection, the unique feature of our approach compared with the therapy to date with monomeric insulins is that insulin analogues consisting of two identical or different insulin monomers covalently linked together via a bridge, where the insulin monomers are selected from the group comprising human insulin and animal insulins and derivatives of the aforementioned insulins, and where at least one of the two insulin monomers of an insulin analogue is a derivative, and physiologically acceptable salts thereof, are used. In particular there is use of insulin analogues in which the C termini of the B chains are truncated and modified in position B26. The insulin monomers can be bridged by substances suitable for linking proteins. Such substances and processes for linking proteins have been known for a long time. In particular, the novel insulin analogues have a bridge which is preferably located between the N-terminal amino groups of the B chains of the two insulin monomers, and which is particularly preferably formed from a linear or branched bifunctional carboxylic acid residue of the formula $(CRR')_n(CO—)_2$ in which n, R, R' are defined as stated below for formula I. Examples of animal insulins are the porcine, monkey, bovine and chicken insulins. Insulin derivatives are derivatives of said insulins which differ by substitution and/or deletion of at least one naturally occurring amino acid residue and/or addition of at least one amino acid residue and/or organic residue from the corresponding, otherwise identical naturally occurring insulin. One example of an insulin derivative monomer is Gly(A21), Arg(B31), Arg(B32) human insulin, and one example of the dimeric insulin analogue of the invention is B1, B1-Sub-[D-Ala$^{B26}$]-des-[B27-B30]-insulin-B26-amide insulin dimer. The insulin analogues can be described in particular by the general formula I:

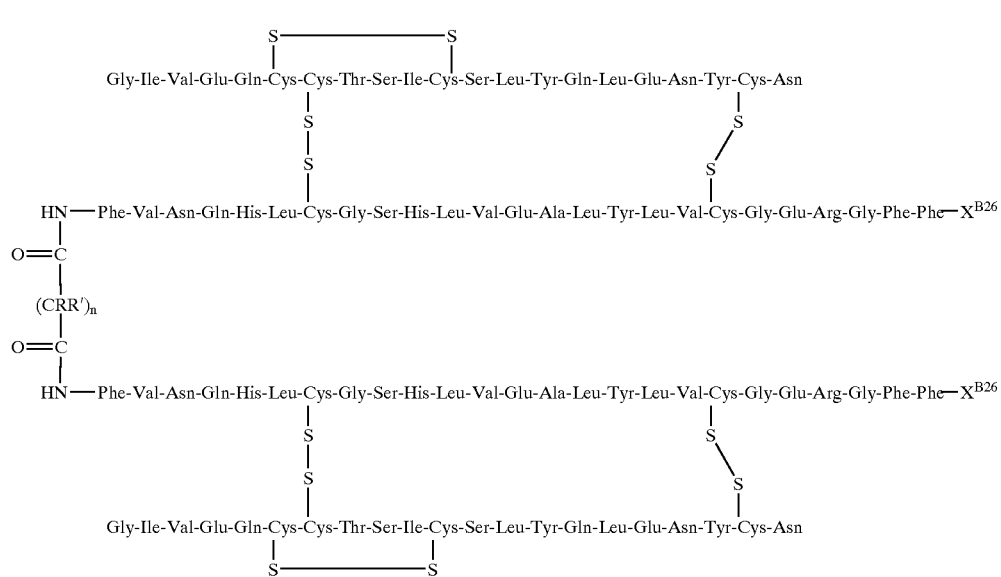

where
- X is, independently of one another, a branched or unbranched $C_1$–$C_{10}$-alkyl group, mono- or polysubstituted aryl group, $C_1$–$C_{10}$-alkyl group, mono- or polysubstituted or unsubstituted O-aryl group, an amino acid or a derivative thereof, or a group of the formula NRR';
- R,R' is H, $NH_2$, a branched or unbranched $C_1$–$C_{10}$-alkyl radical or mono- or polysubstituted or unsubstituted aryl group;
- n is 0, 1, 2, . . . 16.

The invention further relates to insulin analogues of the formula I as described above where X is an amino acid derivative in which the carboxylic acid group is amidated.

The invention further relates to insulin analogues of the formula I as described above where X is the amino acid sarcosine whose carboxylic acid group is amidated.

The invention further relates to insulin analogues of the formula I as described above where the X residues in the two B chains differ from one another.

The invention further relates to insulin analogues of the formula I as described above where X is an amino group.

The invention further relates to a pharmaceutical preparation comprising such insulin analogues. Such a pharmaceutical preparation comprises an insulin analogue of the present invention and a pharmaceutical carrier selected from the group consisting of a zinc salt, phenol, m-cresol, glycerol, and a buffer. The present invention further extends to a method for treating diabetes in a host, comprising administering a pharmaceutical preparation of the present invention to the host, and a process for producing a pharmaceutical preparation for treating diabetes, and a process for preparing the insulin analogues.

The insulin analogues are prepared in a known manner by bridging two optionally partially protected monomeric molecules with the preactivated dicarboxylic acid (A Schüttler, D. Brandenburg, Hoppe Seyler's Z. Physiol. Chem. 1982, 363, pp.317–330). The monomeric analogues can be obtained by enzyme-catalyzed semisynthesis or by methods of genetic manipulation (see examples of the invention).

The invention accordingly further relates to a process for preparing the insulin analogues as described above, where (a) the monomeric insulin analogues are obtained by enzyme-catalyzed semisynthesis or by methods of genetic manipulation, (b) the monomeric insulin analogues from step (a) are optionally partially protected by protective groups;

(c) the protected monomeric insulin analogues from step (b) and/or the monomeric insulin analogues from step (a) are reacted with a preactivated dicarboxylic acid, and (d) the insulin analogues obtained in step (c) are isolated from the reaction mixture.

Compared with human insulin and monomeric insulin analogues, the dimers of the invention are distinguished by particularly high affinity for insulin receptors and superpotency in vitro, the latter up to twenty times the insulin effect.

In contrast to previously disclosed covalent insulin dimers, the novel dimers show very high bioactivities. The ratio of bioactivity to receptor binding is at least 2, and in some cases even 4 to 5. They are thus considerably more biologically effective. Comparison of these quotients with those described in the literature for B1,B1'-suberoyl dimers reveals a factor of at least 11 (0.18:2), and a maximum of 28.

The advantages achieved with the insulin dimers of the invention are, in particular, that 1. compared with insulin and all analogues employed therapeutically at present there is expected to be a relative hepatoselectivity and thus a more physiological mode of action (primary site of action the liver and not the periphery), 2. compared with previously disclosed insulin dimers for the first time a considerably improved biological efficacy is present, 3. the biological activity which is considerably increased compared with insulin and monomeric analogues can prove to be very advantageous on use because an equivalent effect would be achievable with distinctly smaller amounts of active substance.

EXAMPLES OF THE INVENTION

Abbreviations

| | |
|---|---|
| AA | amino acid |
| Ac | acetate ($CH_3COO^-$) |
| Alox | aluminum oxide ($Al_2O_3$) |
| CZE | capillary zone electrophoresis |
| DIPEA | N,N-diisopropylethylamine |
| DMF | dimethylformamide |
| DMSO | dimethyl sulfoxide |
| DOI | desoctapeptide insulin |
| Eq | equivalents |
| Fmoc | 9-fluorenylmethoxycarbonyl |
| HOBt | 1-hydroxybenzotriazole |
| HPCL | high performance liquid chromatography |
| MALDI | matrix-assisted laser desorption/ionization |
| MPLC | medium pressure liquid chromatography |
| Msc | methylsulfonylethoxycarbonyl |
| MW | molecular weight |
| NaOH | sodium hydroxide |
| NMM | N-methylmorpholine |
| RP | reversed phase |
| ONSu | N-oxysuccinimide ester |
| Sar | sarcosine |
| Sub | suberoyl |
| TBTU | 2-(1H-benzotriazol-1-yl)-1,1,3,3-tetramethyluronium tetrafluoroborate |
| TEA | triethylamine |
| TFA | trifluoroacetic acid |
| TOF | time of flight |
| TPCK | tosyl-L-phenylalanyl chloromethyl ketone |
| Tris | tris-(hydroxymethyl)aminomethane |

Example 1 of the Invention

Synthesis of B1,B1'-Sub-[$Sar^{B26}$]-des-(B27-B30)-insulin-B26-amide Insulin Dimer Synthesis of the Tetrapeptide Gly-Phe-Phe-Sar-$NH_2$ The peptide was synthesized on a 4-(2',4'-dimethoxyphenyl-Fmoc-aminomethyl)phenoxy resin using the Fmoc protective group tactic. The Fmoc-amino acid esters used for the coupling were formed by the TBTU/HOBt method and employed in a 3-molar excess based on the nominal loading of the resin. The peptide was synthesized in accordance with the following synthesis protocol:

| No. | Operation | Reagents/solvents | Duration | Repeats |
|---|---|---|---|---|
| 1 | Swelling of the resin | DMF | 1 min. | once |
| 2 | Elimination of the Fmoc group | 20% piperidine in DMF | 6 min. | three times |
| 3 | Washing | DMF | 0.5 min | three times |
| 4 | Washing | 2-propanol | 0.5 min. | twice |
| 5 | Kaiser test* | | | |
| 6 | Swelling of the resin | DMF | 1 min. | once |
| 7 | Coupling of the AA | 3 Eq. Fmoc-AA, 3 eq. each TBTU, HOBt and 4.5 eq. NMM in 5 ml DMF | 45 min. | once |
| 8 | Washing | DMF | 0.5 min. | three times |
| 9 | Washing | 2-propanol | 0.5 min. | twice |
| 10 | Kaiser test* | | | |
| 11 | Swelling of the resin | DMF | 1 min. | once |
| 12 | Blocking of unreacted amino end groups | 400 µl $Ac_2O$ and 200 µl DIPEA in 5 ml DMF | 10 min. | once |
| 13 | Washing | DMF | 0.5 min. | |
| 14 | Washing | 2-propanol | 0.5 min. | |

*continue if the test is positive
**continue if the test is negative; if the test result is positive then repeat steps 6–9.

The peptide was eliminated from the resin by acidolysis through addition of 10 ml of the elimination solution composed of 95% TFA, 4% $H_2O$ and 1% triethylsilane as cation trap. After stirring at room temperature for 2 h, the resin was filtered off and thoroughly washed with dichloromethane. The filtrate was evaporated to dryness.

Further purification of the peptide took place by RP-MPLC column chromatography with a linear 2-propanol gradient (0–40% 2-propanol in 400 ml of each of 0.07% TFA starting buffer and feed buffer). Nucleosil 20-$C_{18}$ was used as stationary phase. The flow rate was 180–200 ml/h (82.6% yield).

Semisynthesis of [$Sar^{B26}$]-des-(B27-B30)-insulin-B26-amide

The insulin with truncated C terminus of the B chain was synthesized by enzymatic coupling of the tetrapeptide to $N^{\alpha A1}$-Msc-des-(B23-B30)-insulin. For this purpose it was initially necessary to degrade native insulin enzymatically to DOI, which was then partially provided with a protective group.

Synthesis of des-(B23-B30)-insulin 300 mg (51.66 µmol) of insulin are taken up in 60 ml of reaction buffer (0.05 M Tris, 1 mmol $CaCl_2$). After the pH has been adjusted to 9.5 with solid Tris, the proteolytic degradation is started by adding 16 mg of TPCK-treated trypsin. Incubation is carried out in a water bath at 37° C. for about 6 h, the reaction being monitored by RP-HPLC. The reaction is stopped by adding 4 ml of glacial acetic acid, and the reaction mixture is concentrated in a rotary evaporator. Working up takes place by initial Sephadex G 25f gel filtration and subsequent Sephadex G 50f gel filtration. The product is lyophilized (73.3% yield).

MW: 4865

Synthesis of $N^{\alpha A1}$-(Msc)-des-(B23-B30)-insulin 300 mg (61.66 µmol) of des-(B23-B30)-insulin are dissolved in 22.5 ml of DMSO with the addition of 225 µl of TEA. While stirring gently, a solution of 18 mg (67.86 µmol) of Msc-ONSu in 5 ml of DMSO is added. After a reaction time of 20 min, the reaction is stopped by adding 750 µl of glacial acetic acid, and the reaction solution is dialyzed against demineralized water at 4° C. for 16 h. The retentate is freeze-dried. For further purification, an ion-exchange chromatography is carried out on SP-Sepharose (pH 3; 350 ml of starting buffer, 350 ml of 0.09 M NaCl feed buffer) and desalting is carried out on Sephadex G 25f. The product is lyophilized (30.8% yield).

MW: 5015.16

Tryptic Coupling of Gly-Phe-Phe-Sar-$NH_2$ to $N^{\alpha A1}$—(Msc)-des-(B23-B30)-insulin 132.75 mg (300 µmol) of Gly-Phe-Phe-Sar-$NH_2$ and 150.45 mg (30 µmol) of $N^{\alpha A1}$-Msc-des-(B23-B30)-insulin are dissolved or suspended in 2 ml of DMF (stirred over Alox), 2 ml of 1,4-butanediol and 400 µl of 0.05 M Ca($CH_3COO$)$_2$ solution. The apparent pH is adjusted to 6.7–7.0 with NMM. Subsequently 23 mg of TPCK-treated trypsin, dissolved in 100 µl of 0.05 M Ca($CH_3COO$)$_2$ solution, are added to the reaction mixture. During the reaction time, the progress of the reaction is followed by RP-HPLC and the pH is checked and readjusted where appropriate with NMM. A conversion of almost 90% can be achieved after 4.5 h. The reaction is stopped by adding 4.5 ml of 30% strength acetic acid. The enzyme, the peptide and other low molecular weight substances are removed by Sephadex G 50f gel chromatography. Unreacted peptide is subsequently purified by RP-MPLC and recovered. Further purification of the insulin derivative takes place by preparative RP-HPCL on a Nucleosil 100–10$C_8$ (2.0 cm diameter, 25.0 cm length with a 5.0 cm precolumn (48.6% yield).

MW: 5290.2

Synthesis of B1,B1'-Sub-[$Sar^{B26}$]-des-(B27-B30)-insulin-B26-amide Insulin Dimer 100 mg (18.9 μmol) of $N^{\alpha A1}$-Msc-[$Sar^{B26}$]-des-(B27-B30)-insulin-B26-amide are dissolved in 400 μl of DMSO, 8.7 μl of DMF and 9.5 μl of NMM with the addition of 5.5 equivalents of HOBt. After 30 min, 0.6 equivalents of suberic acid bis-ONSu ester is added in solid form and stirred for 8–30 h. The entire reaction mixture is taken in 1.5 ml of 10% strength acetic acid with the addition of 300 μl of glacial acetic acid and chromatographed on Sephadex G 50f. The dimer fraction is lyophilized. To eliminate the Msc groups, 100 mg of Msc-protected protein are dissolved in 5 ml of a dioxane/water mixture (2/1, v/v) and cooled to 0° C. 514 μl of 2N NaOH are added and the mixture is stirred at 0° C. for 120 s. The reaction is stopped by adding 2.2 ml of glacial acetic acid. The reaction mixture is gel chromatographed on Sephadex G 25f and lyophilized (11.9% yield).

The characterization of the intermediates and the final product took place by RP-HPLC, acidic CZE and MALDI-TOF mass spectrometry (Table 1).

Tab. 1: Yields, purities according to RP-HPLC, and CZE and masses in the synthesis of B1,B1'-Sub-[$Sar^{B26}$]-des-(B27-B30)-insulin-B26-amide insulin dimer

| Derivative | Yield [%] | Purity [%] by RP-HPLC | CZE | MW [g/mol] calc. | meas. |
|---|---|---|---|---|---|
| Gly-Phe-Phe-Sar-$NH_2$ | 82.6 | 98.5 | >99 | 442.5 | 463.2* |
| A1-Msc-DOI-Gly-Phe-Phe-Sar-$NH_2$ | 48.6 | 95.6 | >99 | 5441.2 | 5439 |
| B1,B1'-Sub-DOI-Gly-Phe-Phe-Sar-$NH_2$ dimer | 14.4 | 90 | >99 | 10,720 | 10,710 |

*adduct with sodium (M = 23)

Example 2 of the Invention

Synthesis of B1,B1'-Sub-[D-$Ala^{B26}$]-des-(B27-B30)-insulin-B26-amide Insulin Dimer Synthesis of this truncated insulin dimer took place in analogy to the synthesis described for example 1 of the invention with the exception that the synthetic tetrapeptide Gly-Phe-Phe-D-Ala-$NH_2$ was used. The corresponding yields, purities and masses are shown in Table 2.

Tab. 2: Yields, purities according to RP-HPLC, and CZE and masses in the synthesis of B1,B1'-Sub-[D-$Ala^{B26}$]-des-(B27-B30)-insulin-B26-amide insulin dimer

| Derivative | Yield [%] | Purity [%] by RP-HPLC | CZE | MW [g/mol] calc. | meas. |
|---|---|---|---|---|---|
| Gly-Phe-Phe-D-Ala-$NH_2$ | 61.6 | 99.1 | >99 | 442.5 | 463.2* |
| A1-Msc-DOI-Gly-Phe-Phe-D-Ala-$NH_2$ | 53.9 | 95.1 | >99 | 5441.2 | 5439.4 |
| B1,B1'-Sub-DOI-Gly-Phe-Phe-D-Ala-$NH_2$ dimer | 11.9 | 88.1 | >99 | 10,720 | 10,713 |

*adduct with sodium

Example 3 of the Invention

Synthesis of B1,B1'-Sub-[$Glu^{B26}$]-des-(B27-B30)-insulin-B26-amide Insulin Dimer Synthesis of this truncated insulin dimer took place in analogy to the synthesis described for example 1 of the invention with the exception that the synthetic tetrapeptide Gly-Phe-Phe-Glu-$NH_2$ was used. The corresponding yields, purities and masses are shown in Table 3.

Tab. 3: Yields, purities according to RP-HPLC, and CZE and masses in the synthesis of B1,B1'-Sub-[$Glu^{B26}$]-des-(B27-B30)-insulin-B26-amide insulin dimer

| Derivative | Yield [%] | Purity [%] by RP-HPLC | CZE | MW [g/mol] calc. | meas. |
|---|---|---|---|---|---|
| Gly-Phe-Phe-Glu-$NH_2$ | 74.9 | 94.5 | >99 | 449.2 | 498.3 |
| A1-Msc-DOI-Gly-Phe-Phe-Glu-$NH_2$ | 38.6 | 95.7 | >99 | 5498.2 | 5497.6 |
| B1,B1'-Sub-DOI-Gly-Phe-Phe-Glu-$NH_2$ dimer | 15.8 | >99 | >99 | 10,826 | 10,833 |

Example 4 of the Invention

Biological Properties for Examples 1–3 of the Invention

The biological properties of the dimers B1,B1'-Sub-[Sar, D-Ala or $Glu^{B26}$]-des-(B27-B30)-insulin-B26-amide dimer, described in examples 1–3 of the invention were determined on the one hand on the basis of the receptor binding, and on the other hand on the basis of the bioactivity in vitro.

The receptor binding was determined by displacement studies on IM-9 lymphocytes. The relative biological activity was determined on cultivated 3T3-L1 adipocytes in the form of the glucose transport. Table 4 shows the binding affinities and the relative biological activities of the synthesized insulin dimers.

Tab. 4: Relative receptor binding (determined on IM-9 lymphocytes) and relative biological activities (determined on cultivated 3T3-L1 adipocytes) of all the insulin dimers compared with native insulin.

| Dimer | Rel. receptor binding [%] | Rel. biol. activity [%] |
|---|---|---|
| B1,B1'-Sub-[Sar$^{B26}$]-des-(B27–B30)-insulin-B26-amide insulin dimer | 412 ± 94.8 | 1957 ± 575 |
| B1,B1'-Sub-[D-Ala$^{B26}$]-des-(B27–B30)-insulin-B26-amide insulin dimer | 357 ± 53.6 | 814 ± 184 |
| B1,B1'-Sub-[Glu$^{B26}$]-des-(B27–B30)-insulin-B26-amide insulin dimer | 176 ± 45.8 | 817.5 ± 224 |

References

1. J. Markussen, S. Havelund, P. Kurtzhals, A. A. Andersen, J. Halstrøm, E. Hasselager, U. D. Larsen, U. Ribel, L. Schäffer, K. Vad, 1. Jonassen, *Diabetologia* 1996, 39, pp. 281–288.
2. European patent EP 0 383 472 B1.
3. S. Gammeltoft, *Physiol Rev.* 1984, 64, p. 1321.
4. A Schüttler, D. Brandenburg, Hoppe Seyler's Z. *Physiol. Chem.* 1982, 363, pp.317–330.
5. M. Weiland, C. Brandenburg, D. Brandenburg, H. G. Joost, *Proc. Natl. Acad. Sci. USA* 1990 87, pp. 1154–1158.
6. M. Breiner, M. Weiland, W. Becker, D. Müller-Wieland, R. Streicher, M. Fabry, H. G. Joost, *Molecular Pharmacology* 1993, 44, pp. 271–276.
7. F. Shojaee-Moradie, N. C. Jackson, M. Boroujerdi, D. Brandenburg, P. H. Sönksen, R. H. Jones, *Diabetologia* 1995, 38, pp. 1007–1013.
8. M. A. Tatnell, R. H. Jones, K. P. Willey, A. Schüttler, D. Brandenburg, *Biochem. J.* 1983, 216, pp. 687–694.

What is claimed is:

1. An insulin analogue consisting of two identical or different insulin monomers covalently linked together via a bridge.

wherein the insulin, monomers are selected from a group consisting of human insulin, an animal insulin a derivative of a human insulin, and a derivative of an animal insulin, wherein at least one derivative of a human insulin or a derivative of an animal insulin is present in said insulin analogue, wherein said insulin analogue has a formula of:

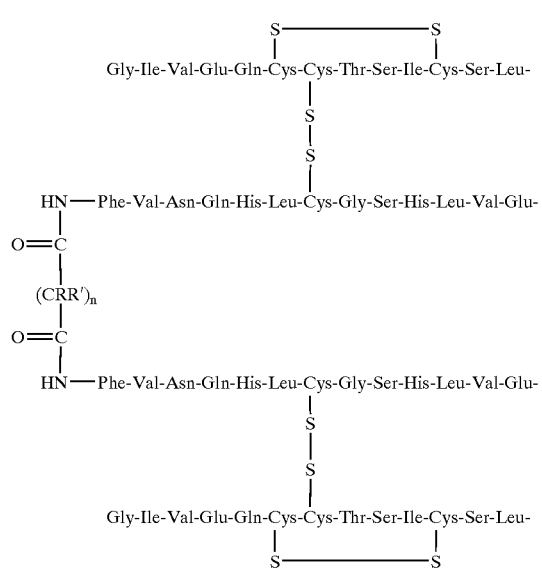

(I)

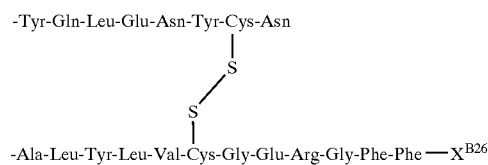

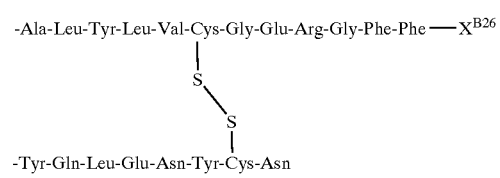

wherein:

a) X is, independently of one another, a branched or unbranched $C_1$–$C_{10}$-alkyl group, a mono- or polysubstituted aryl group, a $C_1$–$C_{10}$-alkyl group, mono- or polysubstituted or unsubstituted O-aryl group, an amino acid, or a group of the formula NRR', wherein b) each of R and R' is H, $NH_2$, a branched or unbranched $C_1$–$C_{10}$-alkyl radical, or a mono- or polysubstituted or unsubstituted aryl group, and wherein c) n is 0, 1, 2, 3, 4, 5, 6, 7, 8, 9, 10, 11, 12, 13, 14, 15, or 16; or a physiologically acceptable salt or said insulin analogue.

2. The insulin analogue as claimed in claim 1, wherein the X residues in the two B chains are different from one another.

3. The insulin analogue as claimed in claim 1, wherein X is an amino group.

4. The insulin analogue as claimed in claim 1, wherein X is an amino acid in which the carboxylic group of said amino acid is amidated.

5. The insulin analogue as claimed in claim 4, wherein X is the amino acid sarcosine.

6. A pharmaceutical preparation, comprising
   a) an insulin analog as claimed in claim 1, and
   b) a pharmaceutical carrier selected from the group consisting of a zinc salt, phenol, m-cresol, glycerol, and a buffer.

7. A method for treating diabetes, comprising administering subcutaneously the pharmaceutical preparation as claimed in claim 6 to a host that has diabetes.

8. B1, B1'-Sub-[Sar$^{B26}$]-des-(B27-B30)-insulin-B26-amide insulin dimer.

9. A pharmaceutical preparation, comprising
   a) an insulin analogue as claimed in claim 8, and
   b) a pharmaceutical carrier selected from the group consisting of a zinc salt, phenol, m-cresol, glycerol, and a buffer.

10. A method for treating diabetes, comprising administering subcutaneously the pharmaceutical preparation as claimed in claim 9 to a host that has diabetes.

11. B1, B1'-Sub-[D-Ala$^{B26}$]-des-(B27-B30)-insulin-B26-amide insulin dimer.

12. A pharmaceutical preparation, comprising
a) an insulin analogue as claimed in claim 11, and
b) a pharmaceutical composition selected from the group consisting of a zinc salt, phenol, m-cresol, glycerol, and a buffer.

13. A method for treating diabetes, comprising administering subcutaneously the pharmaceutical preparation as claimed in claim 12 to a host that has diabetes.

14. B1, B1'-Sub-[Glu$^{B26}$]-des-(B27-B30)-insulin-B26-amide insulin dimer.

15. A pharmaceutical preparation, comprising
a) an insulin analogue as claimed in claim 14, and
b) a pharmaceutical composition selected from the group consisting of a zinc salt, phenol, m-cresol, glycerol, and a buffer.

16. A method for treating diabetes, comprising administering subcutaneously the pharmaceutical preparation as claimed in claim 15 to a host that has diabetes.

* * * * *